United States Patent [19]

Lancer

[11] Patent Number: 5,819,431

[45] Date of Patent: Oct. 13, 1998

[54] FOOT DRYER APPARATUS AND METHOD OF DRYING FEET

[76] Inventor: Harold Lancer, 9735 Wilshire Blvd., Beverly Hills, Calif. 90212

[21] Appl. No.: 781,649

[22] Filed: Jan. 10, 1997

[51] Int. Cl.⁶ .................................................... F26B 19/00
[52] U.S. Cl. .................................. 34/90; 34/202; 34/218; 34/231
[58] Field of Search ................................ 34/88, 90, 508, 34/565, 109, 202, 218, 231, 239; 132/73.5, 73.6, 74.5

[56] References Cited

U.S. PATENT DOCUMENTS

| 3,378,009 | 4/1968 | Peplin | 34/202 X |
| 4,839,483 | 6/1989 | Doyle | 200/302.1 |
| 5,165,181 | 11/1992 | Acosta, Sr. et al. | 34/90 |
| 5,438,764 | 8/1995 | Reppas et al. . | |

Primary Examiner—Henry A. Bennett
Attorney, Agent, or Firm—Lyon & Lyon LLP

[57] ABSTRACT

The foot dryer dispenses heated air under pressure over the entire upper and lower portions of the foot of the user. The dryer includes a dryer housing having a front air baffle unit and a rear air containment unit that defines a foot receiving cavity with the dryer housing. A blower mounts within the dryer housing for delivering a uniform flow of air under pressure onto the top and bottom portions of one's foot safely and effectively. A mist dispenser mounts within the rear air containment unit of the dryer housing and dispenses automatically a mist of particles of a fungus inhibiting agent downwardly onto the user's toes. The dispensed powder facilitates inhibiting the growth of foot fungus, such as athlete's foot. The quantity of the agent dispensed is a selected quantity ranging from a nominal dispensing quantity to a maximum dispensing quantity.

13 Claims, 4 Drawing Sheets

FOOT DRYER APPARATUS AND METHOD OF DRYING FEET

TECHNICAL FIELD

The present invention relates in general to an improved foot dryer and a method of using it. The invention more particularly relates to a portable foot dryer that may be used to help prevent the formation of foot fungus and that can dispense a fungus inhibiting agent according to the novel method of dispensing.

BACKGROUND ART

There have been many types and kinds of foot dryers used to facilitate the prevention of foot fungus and for helping to evaporate residual moisture from the feet of users. For example, see the following U.S. Pat. Nos. 1,413,862; 1,658,489; 2,247,483; 3,711,958; 3,986,643; 4,878,602; 5,003,705; 5,007,182; 5,130,551; 5,157,850; and 5,438,764.

As disclosed in the mentioned patents, various foot dryers blow heated air under pressure onto the foot of a user and dispense a fungus inhibiting agent for helping to prevent the formation of foot fungus. Thus, a user can utilize such foot drying devices to help prevent the formation of foot fungus, such as athletes foot.

While such devices may have been satisfactory for some applications, having a new and improved foot dryer which dries one's foot safely and effectively and then dispenses a desired amount of fungus inhibiting agent efficiently and conveniently would be highly desirable.

U.S. Pat. No. 5,438,746 teaches one attempt to dispense a desired amount of fungus inhibiting agent. In this regard, the disclosed foot dryer includes a raised housing having a perforated top plate for receiving the foot of the user. A series of conduits within the housing is in fluid communication with a blower/heater and powder dispensing unit that dry and dispense respectively. More particularly, the device dispenses a metered amount of powder into one of the conduits. Air under pressure then carries the powder onto the bottom of the toes and foot via the perforation in the top plate.

Though such al device could dry the user's foot and dispense a fungus inhibiting agent, such a device could not be readily and effectively used repeatedly as the dispensed powder could easily and readily accumulated in the apertures of the top plate of the foot dryer. Also, the dispensed powder would be blown into the air causing the surrounding areas around the dryer to be coated with the dispensed powder. Thus, not only would the apertures become easily blocked after repeated use of the dryer, but use of the device would also result in unnecessary and unwanted clean up activities after each use. Moreover, if one used the device straight from a shower or bath, excess fluids would accumulate in the apertures. The dispensed powder would form a paste if users start the dispenser too soon or by mistake before their feet become dry.

Therefore, having a new and improved foot dryer that dries feet safely and effectively and can dispense a fungus inhibiting agent without causing unnecessary and undesired cleaning maintenance is highly desirable. Moreover, such a new and improved drying device should be able to be used repeatedly over long periods without contaminating the areas around the device with dispensed powder.

DISCLOSURE OF INVENTION

Therefore, the principal object of the present invention is to provide a new and improved foot dryer and method of using it to dispense a fungus inhibiting agent in is a safe and effective manner.

Another object of the present invention is to provide such a new and improved foot dryer that helps distribute heated air under pressure uniformly over the entire upper and lower portions of the foot of the user safely and effectively.

Briefly, the above and further objects of the present invention are realized by providing a new and improved foot dryer and method of using it to dispense heated air under pressure over the entire upper and lower portions of the foot of the user according to a novel dispensing method of the present invention.

The foot dryer includes a dryer housing having a front air baffle unit and a rear air containment unit that defines a foot receiving cavity with the dryer housing. A blower mounts within the dryer housing for delivering a uniform flow of air under pressure onto the top and bottom portions of the foot of the user in a safe and effective manner.

A mist dispenser mounts within the rear air containment unit of the dryer housing. It dispenses automatically a mist of particles of a fungus inhibiting agent downwardly onto one's toes. The dispensed powder facilitates inhibiting the growth of foot fungus, such as athlete's foot. The quantity of the agent dispensed is a selected quantity ranging from a nominal dispensing quantity to a maximum dispensing quantity.

BRIEF DESCRIPTION OF DRAWINGS

The above-mentioned and other objects and features of this invention and the manner of attaining them will become apparent, and reference to the following description will best explain the invention itself through an embodiment of the invention, taken in conjunction with the accompanying drawings, wherein.

DETAILED DESCRIPTION OF THE EXEMPLARY EMBODIMENT

Figure 1:
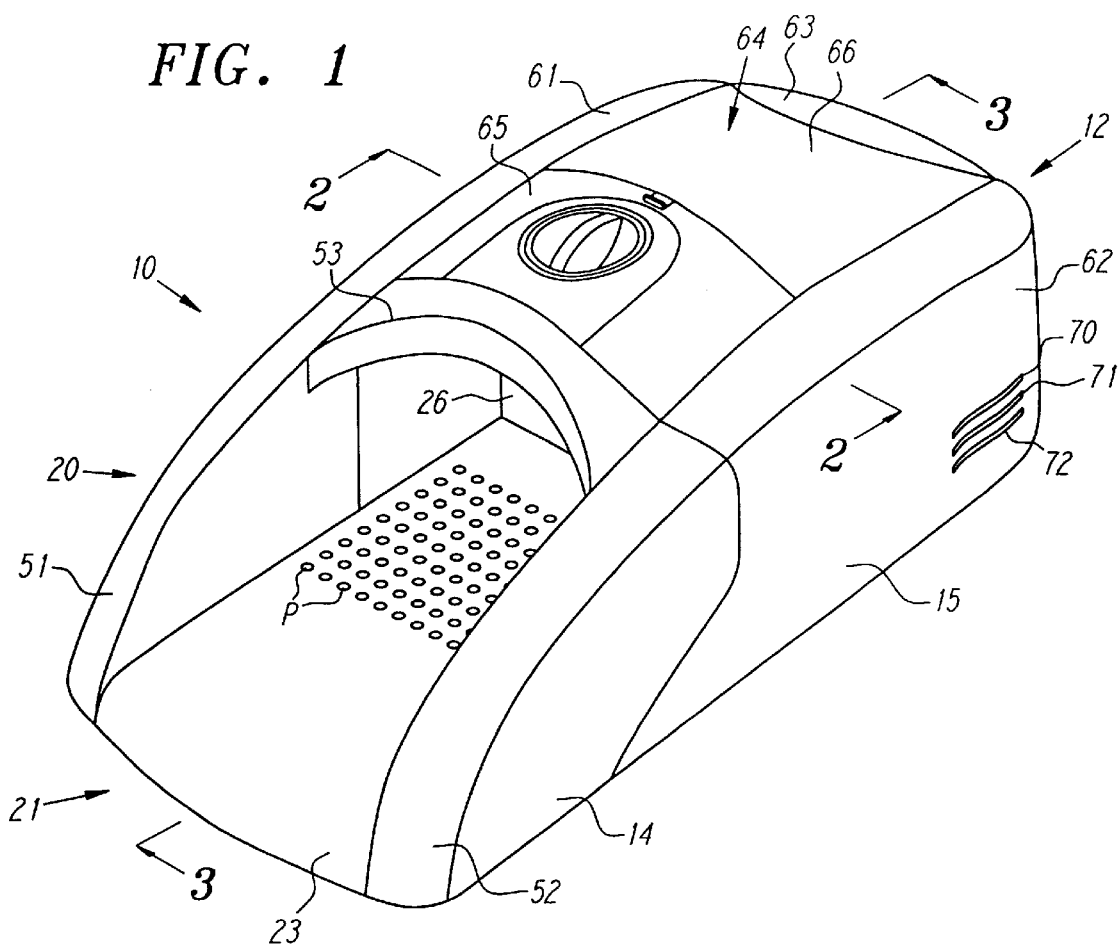
FIG. 1 is a pictorial view of a foot dryer which is constructed in accordance with the present invention.
Figure 2:
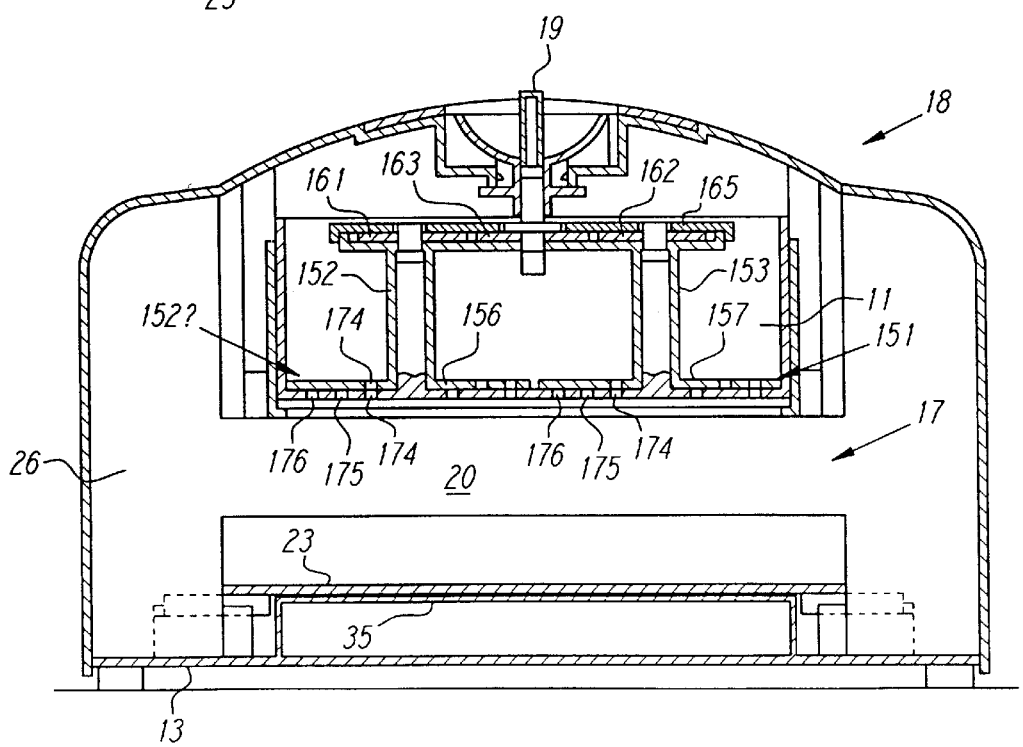
FIG. 2 is a slightly enlarged sectional view of the foot dryer of FIG. 1, taken substantially on line 2—2 thereof.

FIGS. 1–5 show a foot dryer 10, which is constructed according to the present invention. The foot dryer 10 readily distributes warm air uniformly over the foot 16 or feet of a user for drying purposes. In order to help prevent the formation of foot fungus and under user selection and control, the foot dryer also bathes the user's feet with a fine mist of a moisture inhibiting or fungus inhibiting agent 11 (FIG. 2).

The dryer 10 comprises a dryer housing 12, having a generally rectangularly shaped base plate 13 (FIG. 5) for supporting from below a front or upper air baffle unit 14 (FIG. 1) and a rear air containment unit 15. The front and rear units 14 and 15 are secured removably together to define within the dryer housing 12 a foot receiving cavity or space 20 having an entrance way 21. A partition 26 disposed within the cavity 20 functions as a stop for helping one to position his or her toes properly within the cavity 20. The foot receiving cavity 20 is sufficiently large to receive both feet of the user.

Although in the preferred embodiment of the present invention, the foot receiving cavity 20 is sufficiently large to receive both feet of the user, the present invention contemplates a smaller cavity for receiving a single foot.

In accordance with a novel method of cleaning, the front and rear units 14 and 15 can be easily separated from one another to facilitate the cleaning of the dryer 10. This is explained in greater detail below.

Figure 5:
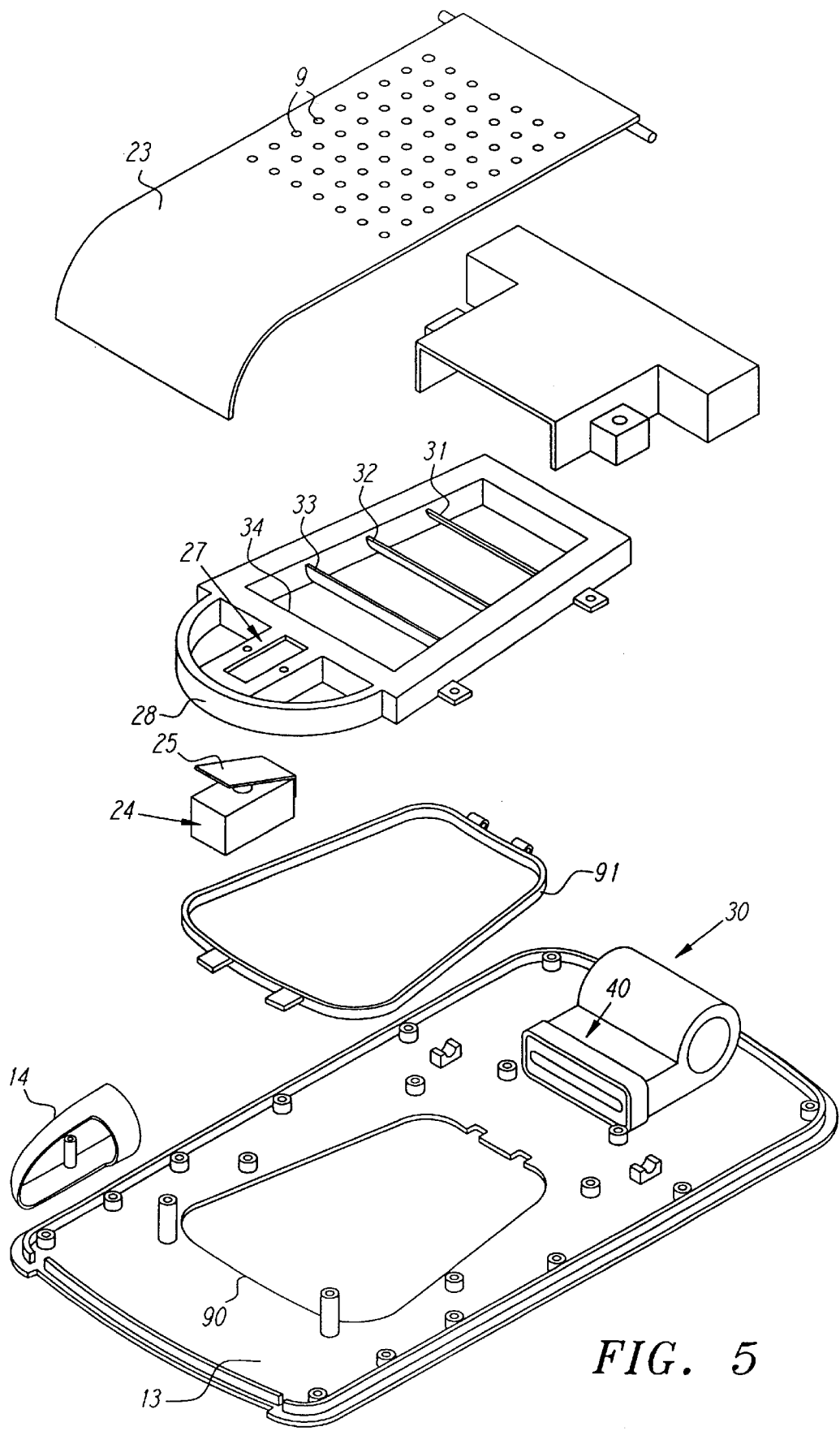
FIG. 5 is an exploded pictorial view of a supporting base forming part of the foot dryer of FIG. 1.

In order to bathe the user's feet with a uniform flow of warm or heated air under pressure, the dryer 10 also includes a blower 30 and a heater 40. Both are disposed within the containment unit 15. Base plate 13 supports the blower 30 and the heater 40 from below (FIG. 5.)

As best seen in FIG. 2, the blower 30 and the heater 40 are in fluid communication with one another and in fluid communication with the cavity 20. In this manner, the blower 30 supplies air under pressure, for helping to distribute a uniform flow of air under pressure within the cavity 20.

A thermostat (not shown) coupled to the heater 40 enables the user to control the temperature of the air under pressure which in turn helps to control the amount of time required to dry the user's feet. In this manner, the user may employ the heater 40 and its associated thermostat to enable warm air under pressure to be distributed to the foot receiving cavity 20.

An electrical cord with an electrical socket male plug (not shown) can be plugged into a source of electrical power for supplying the blower 30 and the heater 40 with electrical energy.

Figure 3:
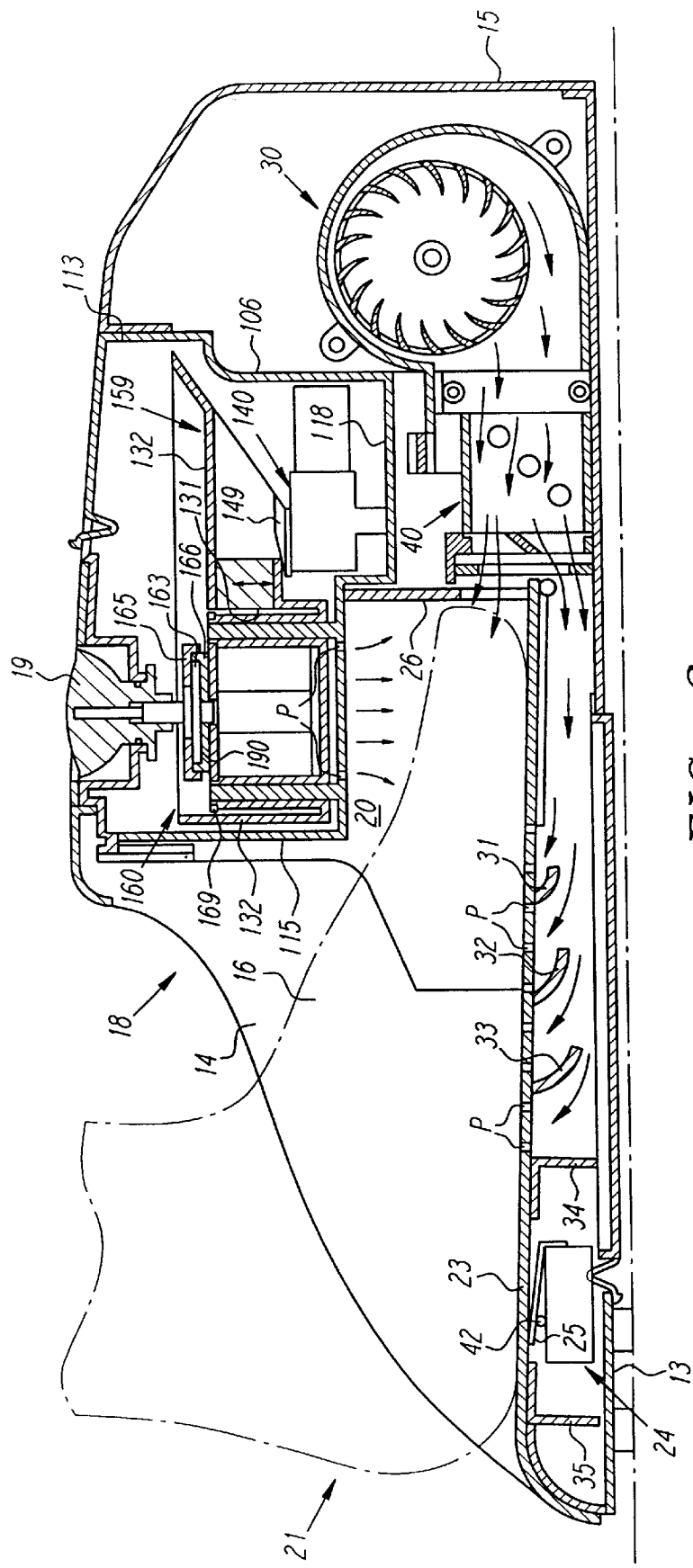
FIG. 3 is a slightly enlarged sectional view of the foot dryer of FIG. 1, taken substantially on line 3—3 thereof.

As best seen In FIGS. 3 and 5, the dryer 10 also includes a mist or powder dispenser 18 having a rate control knob 19. The mist dispenser 18 mounts in the containment unit 15. As will be explained hereinafter in greater detail, the mist dispenser 18 causes the foot or feet of the user to be bathed with a fine mist of airborne particles 17 (FIG. 2) of the moisture or fungi inhibiting agent 11 in accordance with the novel dispensing and drying method of the present invention. In this regard, after the user has dried his or her feet in the dryer 10, the user is able to select, via the control knob 19 a desired amount of the mist particles 17 to be dispensed from the dispenser 18. In this manner, the dispensing of the inhibiting agent 11 helps to promote healthy, fungi free feet as will be explained in greater detail.

To enable the user to activate and deactivate the dryer 10 easily during use, the dryer 10 further includes an enlarged perforated switch plate 23. The switch plate 23 rockably mounts within the dryer housing 12. The perforated switch plate 23 mounts between the front and rear units 14 and 15. It includes small perforations or apertures such as a perforation P. The switch plate perforations, such as the perforation P, are sufficiently large to allow air under pressure to flow upward through them. They are also small enough to help prevent moisture flowing down through them. In this regard, any residual moisture that flows from the feet into a perforation P will be substantially held within the perforation due to its small size. The air under pressure will then quickly evaporate the moisture.

This is an important feature of the present invention as such small perforations help distribute the air uniformly to the bottom portions of the feet and toes of the user and helps to form small droplets of moisture that are easily and quickly evaporated a by the air under pressure as it passes through the perforations P.

A waterproof micro-switch 24 having a depending spring member 25 mounts between the switch plate 23 and a lower portion of bottom air baffle unit 27 that is supported from below by the base plate 13. In this regard, when a sufficient amount of force is applied downwardly on the switch plate 23, the switch plate 23 moves pivotally downwardly to cause the spring member 25 to become fully compressed in engagement with an actuator 42 forming part of the micro-switch 24. The complete compression of the spring member 25 permits the micro-switch 24 to be actuated, which in turn establishes an electrical signal path between the source of electrical power (via the electrical cord) and the blower 30 and the heater 40.

The blower 30 and the heater 40 respond to the electrical power signal to supply the cavity 20 with a uniform flow of air under pressure to facilitate the drying of the user's feet in a fast and efficient manner.

From the foregoing, those skilled in the art should understand that the user controls the temperature of the air being delivered to the foot cavity 20 by use of the thermostat. The user can adjust the thermostat to cause the temperature of the air delivered under pressure to the cavity 20 to change between an off or ambient room temperature and a fully on or maximum temperature depending on the amount of moisture to be evaporated from the user's feet. The user also may use the dryer 10 for bathing his or her feet with the fine mist of particles 17. In this regard, the dispenser 18 is sufficiently efficient to dispense the agent 11 within the cavity 20 in a short period of time between about one second and about one minute depending upon the amount of agent 11 the user desires to have his or her feet bathed with for moisture or fungus inhibiting purposes.

As will be explained in greater detail, the lower air baffle unit 27 is in full fluid communication with the blower 30 and heater 40. The lower air baffle unit 27 includes a curved ribbed frame member 28 (FIG. 5), which has a plurality of evenly spaced apart louvers or ribs 31–33. The louvers 31–33 are of different widths and sizes, and cooperate with the frame 28 and a back rib 34 to cause air passing into the frame member 28 to be evenly distributed into the cavity 20 as it is blown against the perforated switch plate 23. In this manner, the air under pressure flows uniformly into contact and across the bottom portion of the feet and toes of the user when the user is depressing the switch plate 23 downwardly with a sufficient force to activate the switch 24.

In use, the user places one or both of his or her feet into the cavity space 20 of the dryer 10 a sufficient distance to allow the toes of the user to engage the partition 26. The user then moves his or her foot backward to slightly space the toes from the partition bringing the bottom of the feet into engagement with the switch plate 23.

The user then presses the heel of his or her foot or feet downwardly against the switch plate 23 with a sufficient amount of force to cause the switch plate 23 to move rockably downwardly to activate the micro-switch 24. When the micro-switch 24 is activated, the blower 30 supplies the cavity space 20 with a uniform flow of air under pressure via the upper and lower air baffle units 14 and 27 respectively.

If the user desires the drying process to be expedited, the user increases the temperature of the air under pressure by adjusting the thermostat to a desired temperature. When the foot or feet of the user are dry, the user removes his or her extremities from the cavity space 20, which in turn causes the micro-switch 24 to move to its normally open position thereby removing the electrical signal from the blower 30 and the heater 40.

In another embodiment of the present invention, the thermostat 40 is a smart thermostat that automatically controls the temperature of the air under pressure. In this regard, ambient temperature air is delivered to the cavity during a first period of time. During a second period of time the temperature of the air under pressure is increased from the ambient temperature level to a maximum temperature level. Finally, during a third period of time, the temperature of the air under pressure is decreased from the maximum temperature level to the ambient temperature level. In this controlled manner, the temperature of the air under pressure is never maintained at a sufficiently high level to cause the feet and toes of the user to be overly heated. Thus, the feet do not sweat which in turn assures the feet will remain dry for helping to prevent the growth of fungi, such as athlete's foot.

In still yet another embodiment of the present invention, the activation of the micro-switch 24 causes the dispenser 18 to create the fine mist of moisture inhibiting particles 17 after the drying cycle of the dryer has been completed. Such particles remain in the dispenser 18 until the user activates the control knob 19 after the drying cycle has been completed. In this regard, at the end of the above described drying process, the user removes the pressure from the switch plate 23 causing the blower 30 and the heater 40 to be deactivated. At about the same time or simultaneously, the user rotates the control knob 19 to a desired dispensing rate allowing the particles 17 to enter into the cavity space 20. The dispenser 18 operates for a sufficient amount of time of between about 0.5 seconds and about 5 seconds to permit bathing of the foot or feet of the user.

In the event, the user desires an additional amount of bathing to take place after the dispenser 18 has ceased operation, the user may press and release the control knob 19 which in turn will cause the dispenser to manually produce an additional amount of mist particles 17. This manual procedure may be repeated as often as desired to allow the appropriate amount of particle bathing to be accomplished in accordance with the desires of the user.

In this manner, the foot or feet of the user are dried in a fast and efficient manner for prompting healthy feet and if so desired the foot or feet of the user are further bathed with fine mist particles of fungi inhibiting or moisture inhibiting agents to further promote healthy, fungi free feet.

As the particles 17 are dispensed within the cavity 20 at about the rear containment unit 15, the particles 17 remain in the cavity 20 and do not leave the dryer 10. Thus, the area surrounding the dryer 10 is not coated with the powder before, during or after the dispensing cycle.

Considering now the construction of the dryer 10 in greater detail, with reference to FIGS. 1–5, the mist dispenser 18 generally includes an outer powder pan or box 102 having a pair of side wall members 104 and 106, each with a set of integrally connected hollow support legs, such as support legs 108 and 109. The support legs on the side wall members 104 and 106 are slidably received and supported on a corresponding set of upstanding support post members (not shown), that are integrally connected to and extend perpendicularly upward from the base plate 13.

As best seen in FIG. 3, the outer powder pan 102 further includes a pair of end wall members 113 and 115 respectively. The end wall members 113 and 115 are integrally connected to the side wall members 104 and 106 to form a generally rectangularly shaped open box-like configuration with a stair step shaped base or bottom member 116.

The integrally connected base member 116 includes an upper or forward floor member 117 and a lower or rear floor portion 118. The upper member 117 is generally rectangularly shaped and includes a pair of centrally disposed generally overlapping circular shaped cutouts 121 and 122 that help facilitate the dispensing of the inhibiting agent 11 into the cavity 20. In this regard, the cutout 121 and 122 provide a direct passageway P from the dispenser 18 into the cavity 20.

The lower portion 118 is generally rectangularly shaped and supports from below a vibrator 140 that will be described hereinafter.

The vibrator 140 is coupled by a cam member 149 to a pair of agitator members 150 and 151 that respond to the vibrator 140 by moving rapidly up and down in a rectilinear path of travel in the inhibiting agent 11. In this manner the agitators 150 and 151 move up and down in the inhibiting agent 11 to cause it to become airborne in the form of a plurality of small particles, such as the particles 17 that fall under the force of gravity into the cavity 20.

The mist dispenser 18 also includes an inner powder pan or box 130 for holding a reservoir of the inhibiting agent 11. The inner powder box 130 is configured to be received within the outer powder box 102.

The inner powder box 130 has a pair of side wall members 134 and 136 that are integrally connected together at one of the terminal ends by a generally rectangularly shaped end wall member 132.

A base or floor member 138 is integrally connected between the bottom lips of the end wall member 132 and the side wall members 134 and 136 respectively to form an open container for receiving the inhibiting agent 11.

The other terminal ends of the side wall members 134 and 136 are integrally connected to another end wall member 133 that flares outwardly and upwardly at an angle from the base 138. In this regard, the other terminal ends of the side wall members 134 and 136 are triangularly shaped extending upwardly and away from the floor 130 to joining the end wall 133.

As FIG. 3 shows, the end wall member 133 has a centrally disposed hollow boss 159 having a smooth flat front face 191 and a smooth rounded top 192. The boss 159 is sufficiently large to receive a portion of the vibrator 140 when the inner powder box 130 is received within the outer powder box 102.

In order to enable the particles of the inhibiting agent 11 to fall under the force of gravity from the inner powder box 130 through the cutouts 121 and 122 into the cavity 20, the floor member 138 includes a pair of spaced apart upstanding agitator support members 170 and 171. Each support member is surrounded by a set of cutouts or slits, such as the slits 174–176. In this regard, each of the agitators 150 and 151 include hollow spools or spindles 152 and 153 respectively that are slidably received on the support member 170 and 171 respectively to facilitate up and down movement in the inner powder box 130.

The agitators 150 and 151 include powder discs 156 and 157 respectively, at their respective distal ends. Each powder disc includes a corresponding sets of slots, such as slots 177–179. The rotation of the agitators 150 and 151 permit one set of corresponding slits and slots, such as the slit 174 and the slot 177, to be aligned to facilitate dispensing the inhibiting agent 11 at a given rate that is adjustable between a zero flow rate when there is no alignment between slits and slots and a maximum flow rate when the largest slits and slots are aligned, such as the slit 176 and the slot 179.

In order to enable a user to adjust the quantity or flow rate of the particles to be dispensed, the mist dispenser 18 includes a gear box 160 that is coupled between the control knob 19 and the agitators 150 and 151 respectively. The gear box 160 is supported from below by a pair of spaced apart upstanding gear box support members 172 and 173 that extend perpendicularly upwardly from the inner powder box floor 138. The gear box 160 includes a right gear member 161 and a left gear member 162 which are received onto end portions 154 and 155 of the agitators spindles 152 and 153, respectively. The gear members 161 and 162 are spaced apart and interconnected to one another by a central gear member 163 which is coupled to the control knob 19 by a center gear spindle 193.

In this manner, as the user rotates the control knob 19, the central gear member 163 rotates the respective right and left gear members 161 and 162, which in turn rotate the agitators 150 and 151 about their respective support posts 170 and 171 respectively, disposed on the floor 138 of the inner powder box 130. The rotation of the agitators 150 and 151 positions the agitators 150 and 151 and their associated slots relative to individual ones of the slits disposed within the floor member 138, such as the slits 174–176.

Figure 4:
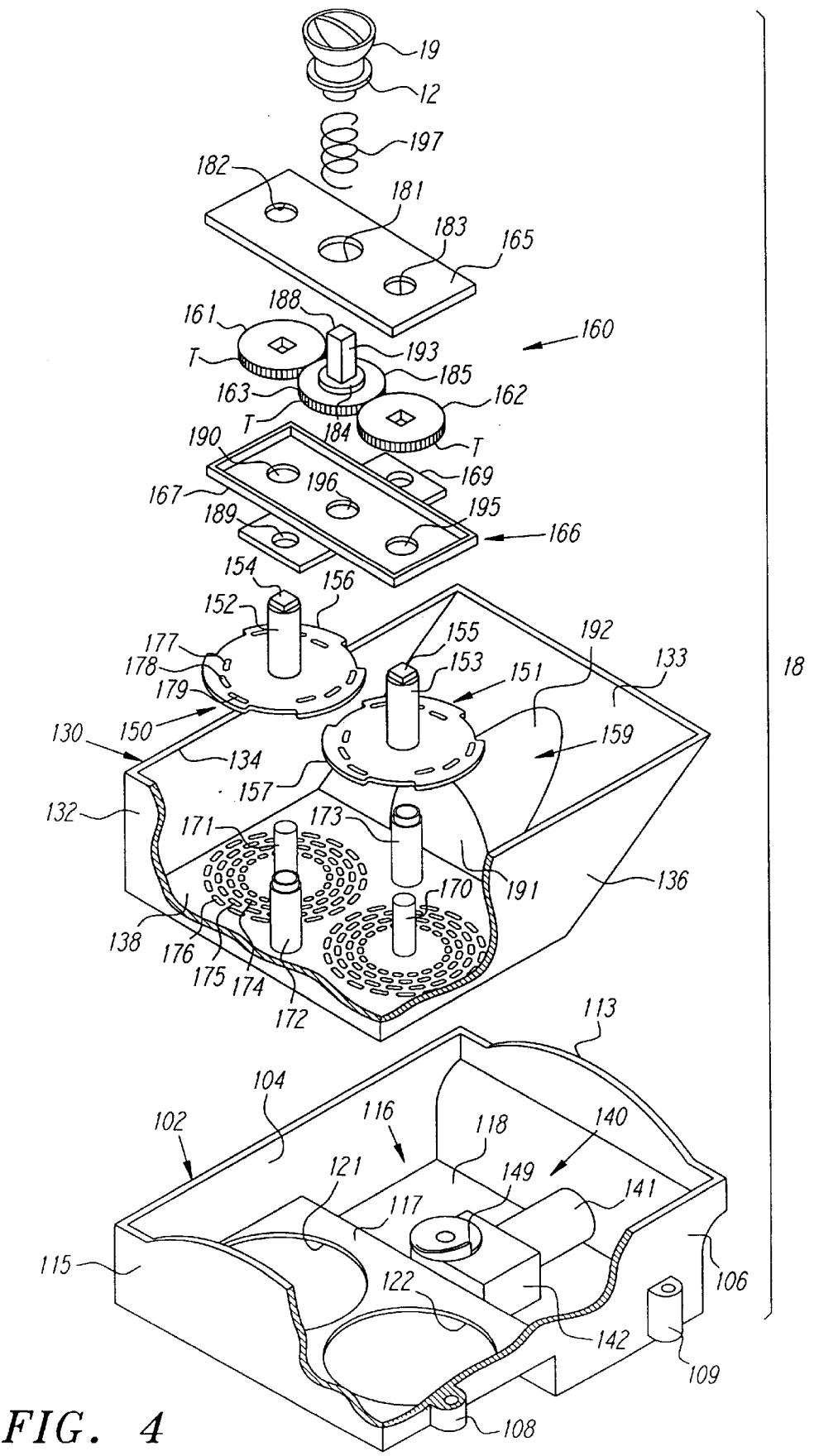
FIG. 4 is a greatly enlarged exploded view of a mist dispenser forming part of the foot dryer of FIG. 1.

Considering now the gear box 160 in greater detail with reference to FIGS. 2 and 4, the gear box 160 generally includes an upper gear cabinet member 165 and a lower cabinet member 166 which are spaced apart from one another by the central gear member 163. In this regard, the central gear member 163 and the right and left gear members 161 and 162 respectively, are disposed in the gear box 160 between the upper cabinet and the lower cabinet members 165 and 166 respectively.

The lower cabinet member 166 includes an upstanding outer wall member 167 that defines a receiving space for the gears 161–163. In this regard, the upper cabinet member 165 sits on the outer wall member 167 to form an enclosed space 190 with the gear box 160.

The gear box 160 also includes a lower support plate 169 for supporting from below the low gear cabinet 166 relative to the inner powder box 130 via the upstanding post members 172 and 173.

The plate 169 includes a pair of holes, such as a hole 189 for receiving the inner powder box posts, such as the post 172.

In order to facilitate the free rotational movement of the gears 161–163 relative to the agitators 150 and 151, the upper cabinet member 165 includes a set of spaced apart spindle holes 182 and 183 respectively. The spindle holes 182 and 183 receive the agitator spindles 152 and 153 respectively. The holes are dimensional so that the spindles rotate with little friction.

A central gear hole 181 is disposed between the spindle holes 182 and 183 and is dimensional for receiving for relatively friction free rotational and up and down movement, the central gear member 163. In this regard, the central gear member 163 includes spaced apart upper and lower circular stops 184 that help sandwich a circular gear 185. The circular gear 185 includes an outer set of teeth (T) that intermesh with like sets of teeth (T) on respective ones of the right and left gears 161 and 162.

As FIG. 4 shows, the hollow post or spool member 193 is centrally disposed and integrally connected to the stops 184, as well as with the gear 185. The spool member 193 is generally box shaped having an open terminal end 188 for receiving in a friction tight fit a corresponding central post 124 forming part of the central knob 19 that will be described hereinafter in greater detail.

To further facilitate the free rotational movement of the gears 161–163 relative to the agitators 150 and 151, lower cabinet member 166 includes another set of spaced apart spindle holes 192 and 193 respectively. The spindle holes 194 and 195 are dimensional for receiving for relatively friction free rotational movement the agitator spindles 152 and 153 respectively.

Another central gear hole 191 is disposed between the spindle holes 194 and 195 and is dimensional for receiving the central gear member 163 for relatively friction free rotational and up and down movement.

A control knob spring 197 mounts around the control knob post 124 and is held in a fixed position between a control knob flange 125 and the upper stop 184 of the central gear member 163.

The vibrator 140, which FIGS. 2 and 3 show in greater detail, includes a vibrator motor 141 and a vibrator gear housing 142.

The motor 141 mounts to the floor of the outer powder box 102 by means not shown and is coupled to the cam member 149 for causing it to rotate about its longitudinal axis. In this regard, the cam rotates about its axis with a sufficient amount of force to cause inner powder box 130 to move up and down which in turn causes the agitators 150 and 151 to move up and down in a rectilinear path of travel through the powder agent 11.

FIGS. 1 and 2 show the front air baffle unit 14 in great detail. The front air baffle unit 14 has a unitary molded plastic construction and generally includes a right leg member 51 and a left leg member 52 which interconnect at one of their respective ends through an intermediate member 53.

The rear air containment unit 15, which FIGS. 1 and 3 show in detail, includes a right side wall member 61, a left side wall member 62, a rear wall member 63 and a top 64, having a front portion 65, and a rear removable cover 66. The rear air containment unit 15 has a unitary molded plastic construction except for the removable cover 67.

Referring to the right and left side wall members 61, 62 in greater detail, each side wall member (such as side wall member 62) includes a set of spaced apart air vents 70–72 that permit atmospheric ambient air to be drawn into the blower 30 for distribution to the cavity 20. The side wall members 61 and 62 are integrally connected at the rear periphery to the rear wall 63 to form an aesthetically pleasing, smooth rounded edge joint.

The base or bottom edge of the rear air baffle unit 27 is configured to interlock with the base plate 13 to form a substantially air tight seal. The interlock allows one to remove the air baffle unit 27 from the base plate 13.

Referring to FIG. 5, the base plate 13 includes a centrally disposed tray-receiving hole 90. The hole is dimensioned for receiving a cleaning tray 91 below the switch plate. The tray 91 collects and holds any residual powder particles, e.g., particles 17, that may fall from one's feet through the perforations P.

While a particular embodiment of the present invention has been disclosed, it is to be understood that various different modifications are possible and are contemplated within the true spirit and scope of the appended claims. Therefore, there is no intention of limitations to the exact abstract or disclosure herein presented. With regard to the attached claims, applicant intends that only claims using the word "means" followed by a statement of function are to be interpreted using 35 U.S.C. § 112, ¶ 6.

I claim:

1. An apparatus for drying an object comprising:

a base plate;

a lower air baffle member supported from below by the base plate for directing and distributing air under pressure substantially upwardly in a plurality of directions to cause an evenly distributed flow of air for facilitating the evaporation of the residual amount of water on the object;

an enlarged, perforated switch plated mounted rockably relative to the base plate and above the lower air baffle member for permitting the distributed flow of air under pressure to pass therethrough to bathe the object with air under pressure for water evaporation purposes;

a water proof switch mounted between the switch plate and the lower air baffle member for generating an electrical signal when the perforated switch plate member is rocked downwardly toward the lower air baffle member;

a blower supported from below by the base plate and responsive to the electrical signal for providing air under pressure to facilitate the evaporation of the residual amount of water on the object;

an upper air baffle member supported from below by the base plate for directing and distributing air under pressure substantially downwardly in a plurality of directions to cause another evenly distributed flow of air for facilitating the evaporation of the residual amount of water on the object;

an air containment housing mounted to the base plate member and cooperating with the upper air baffle member and the enlarged switch plate for helping to define and open drying chamber for receiving therein the object with the residual amount of water thereon;

a heater housing mounted to the base plate;

a heating element mounted within the heater housing for generating thermal energy in response to the electrical signal;

the heater housing having an inlet coupled to the blower for receiving the air under pressure and an outlet coupled to the lower and upper air baffle members for supplying them with heated air under pressure;

a controllable thermostat coupled electrically to the heating element to control the amount of thermal energy generated by the heating element between a selected temperature range of a high temperature and an ambient air temperature;

a holder mounted to the base plate for containing a given quantity of a moisture inhibiting agent;

an agitator mounted within the holder for rapidly displacing the moisture inhibiting agent contained within the holder to cause a fine mist of moisture inhibiting agent particles to be produced;

means defining a passageway between the holder and the drying chamber for permitting the fine mist of moisture inhibiting agent particles to travel into the drying chamber and fall under the force of gravity onto the object to help prevent moisture from forming on the object due to rapid temperature changes within the drying chamber;

the blower including a blower housing mounted to the base plate, an electrical motor mounted to the base plate and responsive to the electrical signal, and a fan coupled to the electrical motor for blower air under pressure from the blower housing to the lower and upper air baffle members; and the object being supported from below on the switch plate and exerting a sufficient force thereon to move the switch plate rockably downwardly a sufficient distance toward the lower air baffle member to actuate the switch to cause the blower to supply air to the drying chamber via the lower and upper air baffle members to cause the residual water on the object to evaporate in a rapid manner.

2. A drying apparatus according to claim 1, wherein the agitator includes:

a motor housing mounted within the holder;

a motor for converting electrical energy into mechanical energy;

at least one agitator disc having a plurality of spaced apart different sized slots disposed therein; and a cam arrangement coupled between the motor and the agitator disc for causing the disc to be pumped up and down in the holder to permit the moisture inhibiting agent to pass through user selected ones of the plurality of spaced apart different sized slots for permitting a controlled amount of the fine mist of moisture inhibiting agent particles to become airborne for delivery to the object when it is disposed within the drying chamber.

3. A drying apparatus according to claim 2, wherein the agitator further includes:

a dispensing rate control arrangement coupled to the agitator disc for manually pumping the disc up and down in the holder to help disburse the moisture inhibiting agent within the holder and for enabling a user to select a given one of the plurality of spaced apart different sized slots for determining the rate at which the fine mist of moisture inhibiting agent particles will be delivered to the object when it is disposed within the drying chamber.

4. A drying apparatus according to claim 3, wherein the dispensing rate control arrangement includes:

a pair of support plates mounted within the holder for securing the disc in a predetermined location within the holder;

a gear arrangement disposed between the support plates and mounted to the disc for enabling the disc to be rotated about its longitudinal axis; and a control knob arrangement including a rotatable control knob coupled to the gear arrangement for enabling a user to rotate the disc selectively between a maximum delivery rate and a minimum delivery rate, where the minimum delivery rate is an off position so that substantially no moisture inhibiting agent is delivered to the object when it is disposed within the drying chamber.

5. A drying apparatus according to claim 4, wherein the gear arrangement includes:

a base support plate mounted to the holder for supporting from below the pair of support plates in a stationary position;

a primary gear disposed between the pair of support plates and coupled to the control knob for facilitating the application of a rotational force to the at least one disc;

a secondary gear disposed between the pair of support plates and coupled between the primary gear and a spindle end portion of the disc to facilitate its rotation about its longitudinal axis; and wherein the pair of support plates each include a pair of spaced apart spindle apertures for receiving therein for relative rotation a spindle portion of the disc and a spindle portion of the control knob.

6. A drying apparatus according to claim 2, wherein the switch plate includes a plurality of perforations, each individual perforation being sufficiently large to permit residual airborne particles of the moisture inhibiting agent to freely pass therethrough but not being sufficiently large to permit residual moisture to freely pass therethrough.

7. A drying apparatus according to claim 2, further comprising:

at least a pair of spacing members mounted to the base plate for helping to define a tray receiving space; and a removable cleaning tray supported from below by the base plate and slidably mounted within the tray receiving space for receiving and holding temporarily residual amounts of the moisture inhibiting agent controllably dispensed within the drying chamber;

the residual amounts of the moisture inhibiting agent falling under the force of gravity within the drying chamber and through the plurality of perforations in the switch plate when the object is not exerting a sufficient force on the switch plate to cause the switch to be activated so that the air under pressure is no longer flowing into the drying chamber.

8. An apparatus for drying an object comprising:

a base plate;

a lower air baffle member supported from below by the base plate for directing and distributing air under pressure substantially upwardly in a plurality of directions to cause an evenly distributed flow of air for facilitating the evaporation of the residual amount of water on the object;

an enlarged, perforated switch plated mounted rockably relative to the base plate and above the lower air baffle member for permitting the distributed flow of air under pressure to pass therethrough to bathe the object with air under pressure for water evaporation purposes;

a water proof switch mounted between the switch plate and the lower air baffle member for generating an electrical signal when the perforated switch plate member is rocked downwardly toward the lower air baffle member;

a blower supported from below by the base plate and responsive to the electrical signal for providing air under pressure to facilitate the evaporation of the residual amount of water on the object;

an upper air baffle member supported from below by the base plate for directing and distributing air under pressure substantially downwardly in a plurality of directions to cause another evenly distributed flow of air for facilitating the evaporation of the residual amount of water on the object;

an air containment housing mounted to the base plate member and cooperating with the upper air baffle member and the enlarged switch plate for helping to define and open drying chamber for receiving therein the object with the residual amount of water thereon;

a heater housing mounted to the base plate;

a heating element mounted within the heater housing for generating thermal energy in response to the electrical signal;

the heater housing having an inlet coupled to the blower for receiving the air under pressure and an outlet coupled to the lower and upper air baffle members for supplying them with heated air under pressure;

a controllable thermostat coupled electrically to the heating element to control the amount of thermal energy generated by the heating element between a selected temperature range of a high temperature and an ambient air temperature;

at least a pair of spacing members mounted to the base plate for helping to define a tray receiving space;

a removable cleaning tray supported from below by the base plate and slidably mounted within the tray receiving space for receiving and holding temporarily residual amounts of a moisture inhibiting agent falling under the force of gravity within the drying chamber and through the plurality of perforations in the switch plate when the object is not exerting a sufficient force on the switch plate to cause the switch to be activated;

the blower including a blower housing mounted to the base plate, an electrical motor mounted to the base plate and responsive to the electrical signal, and a fan coupled to the electrical motor for blower air under pressure from the blower housing to the lower and upper air baffle members; and the object being supported from below on the switch plate and exerting a sufficient force thereon to move the switch plate rockably downwardly a sufficient distance toward the lower air baffle member to actuate the switch to cause the blower to supply air to the drying chamber via the lower and upper air baffle members to cause the residual water on the object to evaporate in a rapid manner.

9. A drying apparatus according to claim 8, further comprising:

a holder mounted to the base plate for containing a given quantity of the moisture inhibiting agent;

an agitator mounted within the holder for rapidly displacing the moisture inhibiting agent contained within the holder to cause a fine mist of moisture inhibiting agent particles to be produced;

means defining a passageway between the holder and the drying chamber for permitting the fine mist of moisture inhibiting agent particles to travel into the drying chamber and fall under the force of gravity onto the object to help prevent moisture from forming on the object due to rapid temperature changes within the drying chamber.

10. A drying apparatus according to claim 9, wherein the agitator includes:

a motor housing mounted within the holder;

a motor for converting electrical energy into mechanical energy;

at least one agitator disc having a plurality of spaced apart different sized slots disposed therein; and a cam arrangement coupled between the motor and the agitator disc for causing the disc to be pumped up and down in the holder to permit the moisture inhibiting agent to pass through user selected ones of the plurality of spaced apart different sized slots for permitting a controlled amount of the fine mist of moisture inhibiting agent particles to become airborne for delivery to the object when it is disposed within the drying chamber.

11. A drying apparatus according to claim 10, wherein the agitator further includes:

a dispensing rate control arrangement coupled to the agitator disc for manually pumping the disc up and down in the holder to help disburse the moisture inhibiting agent within the holder and for enabling a user to select a given one of the plurality of spaced apart different sized slots for determining the rate at which fine mist of moisture inhibiting agent particles will be delivered to the object when it is disposed within the drying chamber.

12. A drying apparatus according to claim 11, wherein the gear arrangement includes:

a base support plate mounted to the holder for supporting from below the pair of support plates in a stationary position;

a primary gear disposed between the pair of support plates and coupled to the control knob for facilitating the application of a rotational force to the at least one disc;

a secondary gear disposed between the pair of support plates and coupled between the primary gear and a spindle end portion of the disc to facilitate its rotation about the longitudinal axis; and wherein the pair of support plates each include a pair of spaced apart spindle apertures for receiving therein for relative rotation a spindle portion of the disc and a spindle portion of the control knob.

13. A drying apparatus according to claim 8, wherein the switch plate includes a plurality of perforations, each individual perforation being sufficiently large to permit residual airborne particles of the moisture inhibiting agent to freely pass therethrough but not being sufficiently large to permit residual moisture to freely pass therethrough.

* * * * *